US010859730B2

(12) United States Patent
Raman et al.

(10) Patent No.: US 10,859,730 B2
(45) Date of Patent: Dec. 8, 2020

(54) MACHINE-LEARNING-BASED MODELS FOR PHASE EQUILIBRIA CALCULATIONS IN COMPOSITIONAL RESERVOIR SIMULATIONS

(71) Applicant: Saudi Arabian Oil Company, Dhahran (SA)

(72) Inventors: Vinay Raman, Lexington, MA (US); Todd R. Ferguson, Malden, MA (US)

(73) Assignee: Saudi Arabian Oil Company, Dhahran (SA)

( * ) Notice: Subject to any disclaimer, the term of this patent is extended or adjusted under 35 U.S.C. 154(b) by 366 days.

(21) Appl. No.: 15/879,793

(22) Filed: Jan. 25, 2018

(65) Prior Publication Data

US 2019/0227191 A1    Jul. 25, 2019

(51) Int. Cl.
| | | |
|---|---|---|
| G01V 99/00 | (2009.01) | |
| G06N 3/08 | (2006.01) | |
| G01N 33/28 | (2006.01) | |
| G01N 33/24 | (2006.01) | |
| E21B 49/08 | (2006.01) | |
| G06N 3/04 | (2006.01) | |

(52) U.S. Cl.
CPC ............ *G01V 99/005* (2013.01); *E21B 49/08* (2013.01); *E21B 49/088* (2013.01);
(Continued)

(58) Field of Classification Search
None
See application file for complete search history.

(56) References Cited

U.S. PATENT DOCUMENTS 7,822,554 B2 * 10/2010 Zuo .................... G01N 33/2823
175/40
7,966,273 B2    6/2011 Hegeman et al.
(Continued)

FOREIGN PATENT DOCUMENTS

WO    WO-2012121769 A2 *  9/2012  ............. G01V 1/282

OTHER PUBLICATIONS

Drohm et al. "On the Quality of Data from Standard Gas-Condensate PVT Experiments" SPE 17768, pp. 525-536, 1998. (Year: 1998).*
(Continued)

*Primary Examiner* — Roy Y Yi
(74) *Attorney, Agent, or Firm* — Fish & Richardson P.C.

(57) ABSTRACT

Technologies related to training machine-learning-based surrogate models for phase equilibria calculations are disclosed. In one implementation, an equation of state (EOS) for each of one or more regions of a reservoir is determined based on results of one or more pressure, volume, or temperature (PVT) experiments conducted on samples of downhole fluids obtained from one or more regions of the reservoir. Compositions of the samples of the downhole fluids are determined and spatially mapped based on interpolations between the one or more regions of the reservoir. One or more PVT experiments are simulated for the spatially mapped compositions of the downhole fluids using the determined EOS to create a compositional database of the reservoir. One or more machine-learning algorithms are trained using the compositional database, and the trained one or more machine-learning algorithms are used to predict phase stability and perform flash calculations for compositional reservoir simulation.

20 Claims, 6 Drawing Sheets

(52) U.S. Cl.
CPC ....... *G01N 33/241* (2013.01); *G01N 33/2823* (2013.01); *G06N 3/08* (2013.01); *E21B 49/0875* (2020.05); *E21B 2200/22* (2020.05); *G01V 99/00* (2013.01); *G06N 3/04* (2013.01)

(56) References Cited

U.S. PATENT DOCUMENTS

| | | |
|---|---|---|
| 9,164,191 B2 | 10/2015 | Dogru |
| 2002/0177986 A1 | 11/2002 | Moeckel et al. |
| 2007/0282582 A1 | 12/2007 | Saaf |
| 2009/0288881 A1 | 11/2009 | Mullins et al. |
| 2015/0073762 A1 | 3/2015 | Patacchini et al. |
| 2017/0075028 A1 | 3/2017 | Bang et al. |

OTHER PUBLICATIONS

Suzuki et al. ("A Distance-based Prior Model Parameterization for Constraining Solutions of Spatial Inverse Problems", Math GeoSci (2008) 40: 4 (Year: 2008).*

Abass (Determination of Cricondentherm, Cricondenbar and Critical Points of Natural Gases Using Artificial Neural Networks, Dec. 2009) (Year: 2009).*

International Search Report and Written Opinion issued in International Application No. PCT/US2019/014696 dated Apr. 29, 2019, 14 pages.

Gaganis et al., "Machine Learning Methods to Speed up Compositional Reservoir Simulation," SPE Europec/EAGE Annual Conference, Copenhagen, Denmark, Jun. 4-7, 2012, published Jan. 1, 2012, 11 pages.

Gaganis et al., "Non-iterative phase stability calculations for process simulation using discriminating functions," Fluid Phase Equilibria, Jan. 25, 2012, 9 pages.

Gaganis et al., "An integrated approach for rapid phase behavior calculations in comsotional modeling," Journal of Petroleum Science and Engineering, Jun. 2014, 14 pages.

Gulf Cooperation Council Examination Report issued in GCC Application No. GC 2019-36909 dated Apr. 16, 2020, 4 pages.

* cited by examiner

MACHINE-LEARNING-BASED MODELS FOR PHASE EQUILIBRIA CALCULATIONS IN COMPOSITIONAL RESERVOIR SIMULATIONS

TECHNICAL FIELD

This disclosure relates to compositional reservoir simulation, and more particularly to phase behavior calculation.

BACKGROUND

Thermodynamic calculations are often employed in compositional reservoir simulations. The calculations can include stability analysis of a hydrocarbon phase, followed by phase-split calculations when the hydrocarbon phase is found to be in the two-phase region in the stability analysis. Both the stability analysis and the phase-split calculations can be iterative processes. They can be performed within other iterative calculations of the compositional reservoir simulations such as in the calculation of the residual and Jacobian calculations.

SUMMARY

The present disclosure describes methods and systems, including computer-implemented methods, computer program products, and computer systems for training machine-learning-based surrogate models for phase equilibria calculations.

In an implementation, an equation of state (EOS) for each of one or more regions of a reservoir is determined based on results of one or more pressure, volume, or temperature (PVT) experiments conducted on samples of downhole fluids obtained from one or more regions of the reservoir. Compositions of the samples of the downhole fluids are determined. The determined compositions of the samples of the downhole fluids are spatially mapped based on interpolations between the one or more regions of the reservoir. One or more PVT experiments are simulated for the spatially mapped compositions of the downhole fluids using the determined EOS to create a compositional database of the reservoir. One or more machine-learning algorithms are trained using the compositional database, and the trained one or more machine-learning algorithms are used to predict phase stability and perform flash calculations for compositional reservoir simulation.

The previously described implementation is implementable using a computer-implemented method; a non-transitory, computer-readable medium storing computer-readable instructions to perform the computer-implemented method; and a computer-implemented system comprising a computer memory interoperably coupled with a hardware processor configured to perform the computer-implemented method/the instructions stored on the non-transitory, computer-readable medium.

The subject matter described in this specification can be implemented in particular implementations, so as to realize one or more of the following advantages. First, the training of the machine-learning based surrogate models is faster because it is based on a reservoir-specific compositional database generated by simulating physical processes (for example, depletion) that occur inside the reservoir. Second, the surrogate models are more accurate and more efficient. Third, the surrogate model uses less memory because only the most relevant tie-lines, representing physical processes that would occur during the oil recovery process for the reservoir, are stored. Other advantages will be apparent to those of ordinary skill in the art.

The details of one or more implementations of the subject matter of this specification are set forth in the Detailed Description, the Claims, and the accompanying drawings. Other features, aspects, and advantages of the subject matter will become apparent from the Detailed Description, the Claims, and the accompanying drawings.

DESCRIPTION OF DRAWINGS

Like reference numbers and designations in the various drawings indicate like elements.

DETAILED DESCRIPTION

The following detailed description describes training machine-learning-based surrogate models for phase equilibria calculations, and is presented to enable any person skilled in the art to make and use the disclosed subject matter in the context of one or more particular implementations. Various modifications, alterations, and permutations of the disclosed implementations can be made and will be readily apparent to those of ordinary skill in the art, and the general principles defined in the present disclosure can be applied to other implementations and applications, without departing from scope of the disclosure. In some instances, details unnecessary to obtain an understanding of the described subject matter can be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Thermodynamic calculations are often employed in compositional reservoir simulations. The calculations can include stability analysis of a hydrocarbon phase, followed by phase-split calculations when the hydrocarbon phase is found to be in the two-phase region in the stability analysis. Both the stability analysis and the phase-split calculations can be iterative processes. They can be performed within other iterative calculations of the compositional reservoir simulations, such as in the calculation of the residual and Jacobian calculations.

The present disclosure describes technologies to evaluate thermodynamic properties and their derivatives for calculating the residual and Jacobian. The technologies are based on machine-learning methods to develop surrogate models for stability analysis and phase-split calculations that are non-iterative. The machine-learning methods can use compositional data of fluids sampled across a reservoir and experimental data based on experiments conducted on sampled fluids to tune an equation of state (EOS) specific to different regions of the reservoir. A database of region-specific pseudo-components can then be created based on the compositional data samples and experimental data. Example experiments can include differential liberation (DL), constant mass expansion (CME), and density measurements. A compositional map is then used to create a database of compositions to train the machine-learning algorithm for performing fast and accurate compositional reservoir simulations.

The workflow for developing machine-learning based surrogate models can include four high-level stages. First, available data on pressure, volume, temperature (PVT) experiments is used to tune the EOS. Region-specific pseudo-components, that are unique to different sectors or regions of the reservoir, are developed and stored in a pseudo-component database. Second, spatial mapping of fluid compositions is performed using downhole fluid sampling and interpolation techniques to create a reservoir-specific compositional map. Third, the region-specific tuned EOS is used to simulate DL tests, constant vapor depletion (CVD) tests, and swelling tests for fluid compositions sampled from the compositional map. Fourth, the results of the simulations are used to train the machine-learning algorithm. The machine-learning algorithm can then provide predictions for thermodynamic properties to be used in compositional reservoir simulations.

Figure 1:
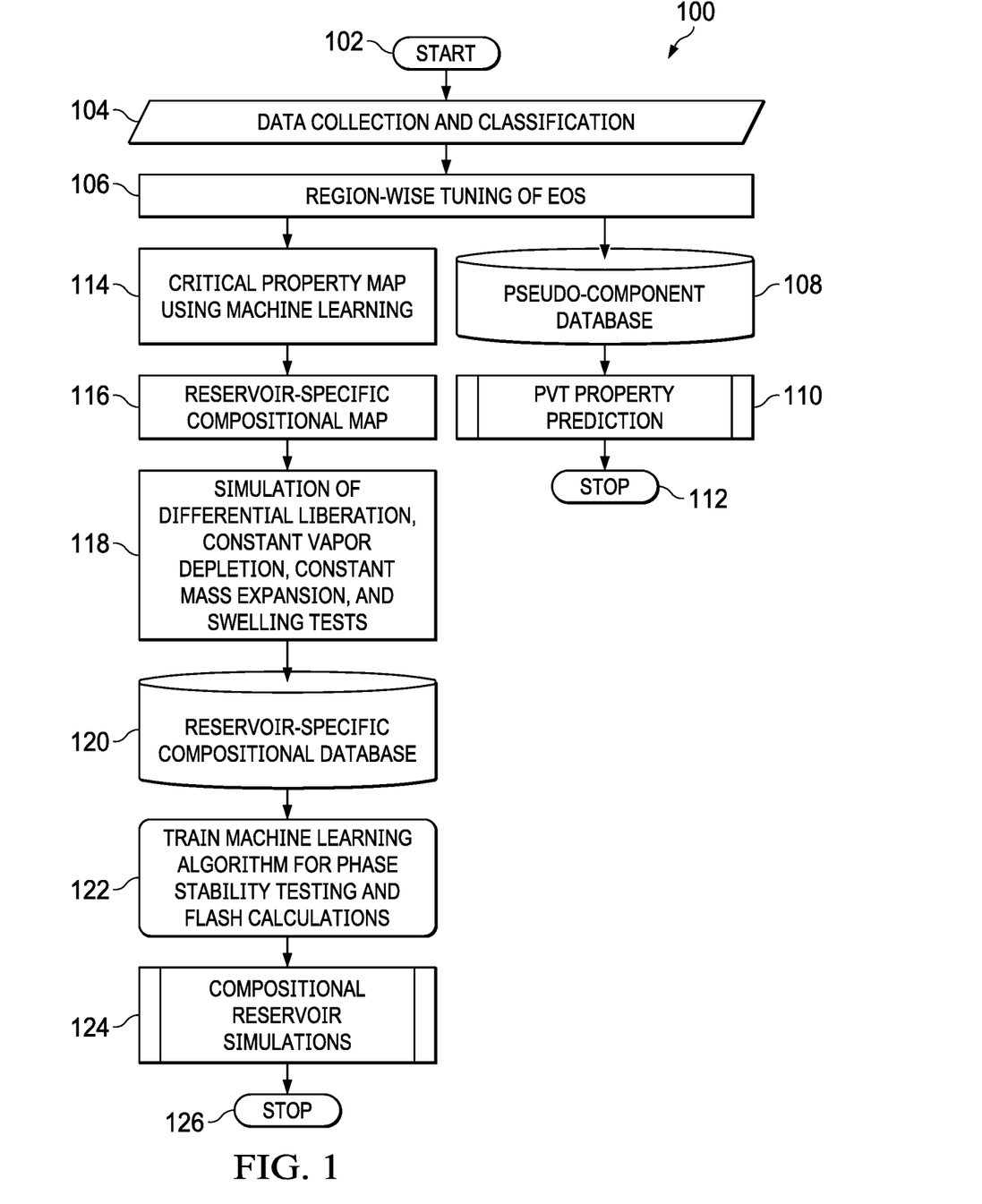
FIG. 1 is a flowchart illustrating an example method of compositional reservoir simulations, according to some implementations of the present disclosure.

FIG. 1 is a flowchart illustrating an example method 100 of compositional reservoir simulations, according to some implementations of the present disclosure. For clarity of presentation, the description that follows generally describes method 100 in the context of the other figures in this description. However, it will be understood that method 100 may be performed, for example, by any suitable system, environment, software, and hardware, or a combination of systems, environments, software, and hardware, as appropriate. In some cases, various steps of method 100 can be run in parallel, in combination, in loops, or in any order.

The method 100 starts at 102. At 104, data collection and classification are performed. In some implementations, the data to be collected can include available data on experiments conducted on fluids obtained from downhole fluid analysis at different well locations in the reservoir. The collected data is classified and used to tune the EOS that match the experimental data.

At 106, region-wise tuning of the EOS is performed. The region-wise tuning of the EOS can be based on results of experiments such as DL, CME, and fluid measurements conducted on sampled fluids obtained from downhole fluid analysis. The region-wise tuning of the EOS can include determining the critical properties of components by regressing data from PVT experiments with results of PVT simulation performed using EOS. The PVT experiments can include DL, CME, and fluid density measurements conducted on sampled fluids obtained from downhole fluid analysis. Example EOS can include Peng-Robinson and Soave-Redlich-Kwong EOS. The critical properties can include critical temperature ($T_c$), critical pressure ($P_c$), and acentric factor ($\omega$).

The relationships between critical temperature, critical pressure, and acentric factor of a pure component i that has a CN greater than 10 and less than 45 can be expressed as:

$$T_{c,i} = A_T e^{B_T \omega_i} \quad (1),$$

and $$P_{c,i} = A_P e^{B_P \omega_i} \quad (2),$$

where the parameters $A_T$, $B_T$, $A_P$, and $B_P$ are fitting parameters determined by fitting $T_c$ and $P_c$ of pure components with a CN greater than 10 and less than 45 using equations (1) and (2). Heavy components with a CN greater than 10 can be lumped together as a single component.

Figure 7A:
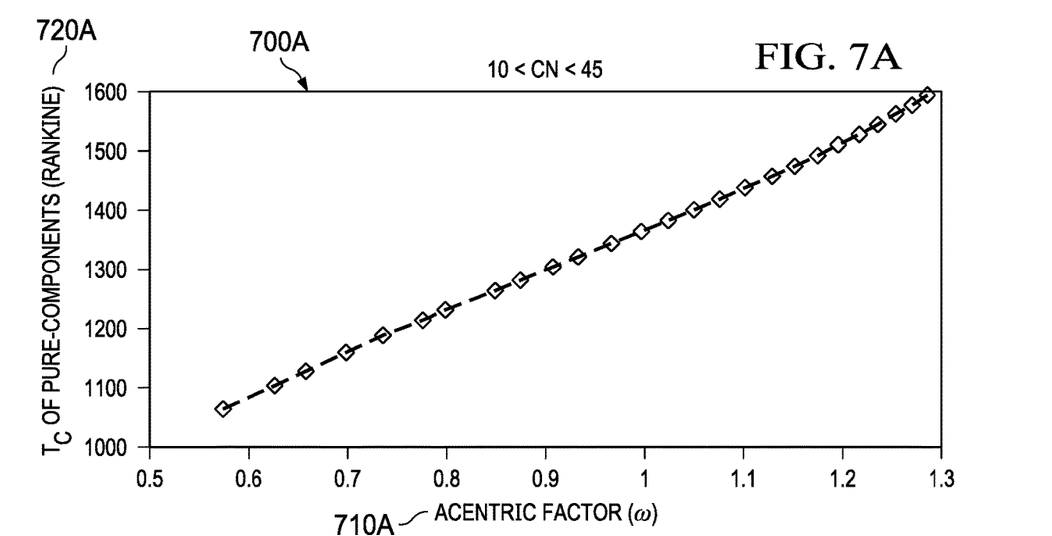
FIG. 7A is a schematic diagram showing an example relationship between critical temperature and acentric factor, according to some implementations of the present disclosure.
Figure 7B:
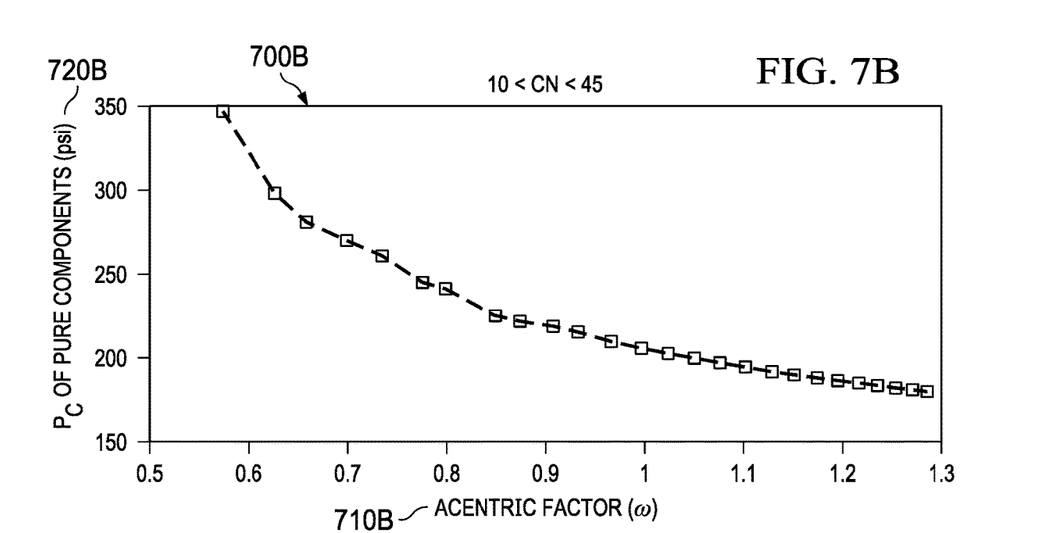
FIG. 7B is a schematic diagram showing an example relationship between critical pressure acentric, according to some implementations of the present disclosure.

Briefly referring to FIGS. 7A and 7B. FIG. 7A is a schematic diagram showing an example relationship 700A between critical temperature and acentric factor, according to some implementations of the present disclosure. FIG. 7B is a schematic diagram showing an example relationship 700B between critical pressure acentric factor, according to some implementations of the present disclosure. The example relationships 700A, 700B are developed for pure components with CN greater than 10 and less than 45. As shown in FIG. 7A, the acentric factor ($\omega$) 710A is positively proportional to the critical temperature $T_c$. As shown in FIG. 7B, the acentric factor ($\omega$) 710B is negatively proportional to the critical pressure $P_c$.

The relationships between the critical temperature ($T_{c,mix}$), critical pressure ($P_{c,mix}$), and acentric factor ($\omega_{mix}$) of the pseudo component can be expressed as:

$$T_{c,mix} = A_T e^{B_T \omega_{mix}} \quad (3),$$

and $$P_{c,mix} = A_P e^{B_P \omega_{mix}} \quad (4).$$

In one-step tuning, the parameter $\omega_{mix}$ is tuned to match the experimental results of DL and CME. The critical parameters $T_{,mix}$ and $P_{c,mix}$ of the pseudo component are obtained from equations (3) and (4), respectively. Equations (3) and (4) can be derived using logarithmic mixing rules for the critical temperature and critical pressure, and using linear mixing rule for the acentric factor. In some cases, an additional step of the tuning process can be performed. The values of $T_{c,mix}$, $P_{c,mix}$ and $\omega_{mix}$ obtained from the one-step tuning can be used as initial estimates to further reduce the error between the experimental results and simulations.

For heavy crude oils that contain components with a CN greater than 45, the same one-step tuning strategy can be extended by using at least two pseudo components. One of the at least two pseudo components can represent the components with CN>45. The other pseudo-component can represent pure components with 10<CN<45. In some cases, two additional equations similar to equation 1 and equation 2 can be used for pseudo-component corresponding to heavy components with CN>45.

Figure 2:
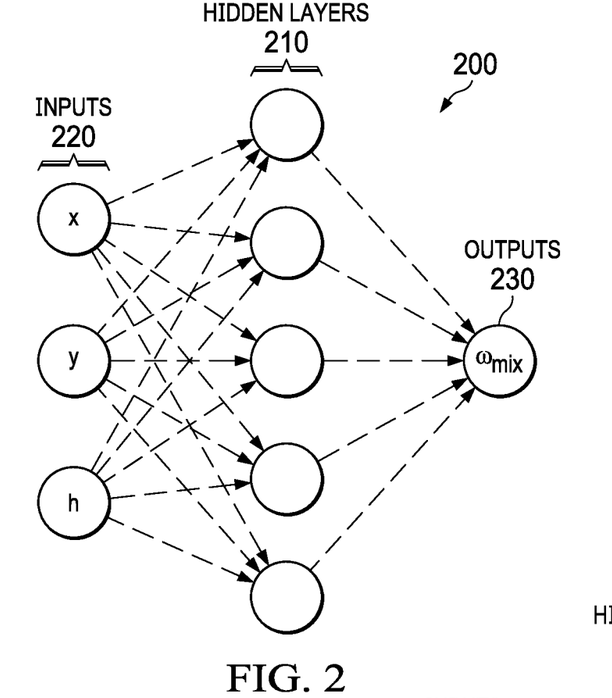
FIG. 2 is a schematic diagram illustrating an example map of critical properties for a one-step tuning method using machine-learning, according to some implementations of the present disclosure.

Referring briefly to FIG. 2, FIG. 2 is a schematic diagram illustrating an example map 200 of critical properties for a one-step tuning method using machine-learning, according to some implementations of the present disclosure. An artificial neural network (ANN) can be developed as a hidden layer 210 for calculating the acentric factor, $\omega_{mix}$. The critical parameters $T_{c,\ mix}$, and $P_{c,\ mix}$ can be obtained based on equations (3) and (4). The input 220 to the ANN algorithm are spatial coordinates x, y, and h of the corresponding region in the reservoir. The output 230 is the acentric factor of the pseudo-component with a CN greater than 10.

Referring back to FIG. 1, in some implementations, regressed pseudo-components that are region-specific can be obtained and stored in a regions-specific, pseudo-component database 108 for PVT property predictions at 110. For example, a region-specific pseudo-component obtained for a region in the neighborhood of location $(x_1, y_1, h_1)$ in sector 1 of a Ghawar field can be stored as "PSC-Sector1-Ghawar". In some cases, PVT property predictions 110 for sector 1 using region-specific pseudo-component can be more accurate than the predictions using generic pseudo-components obtained using all the available PVT data. After 110, method 100 stops at 112.

Figure 3:
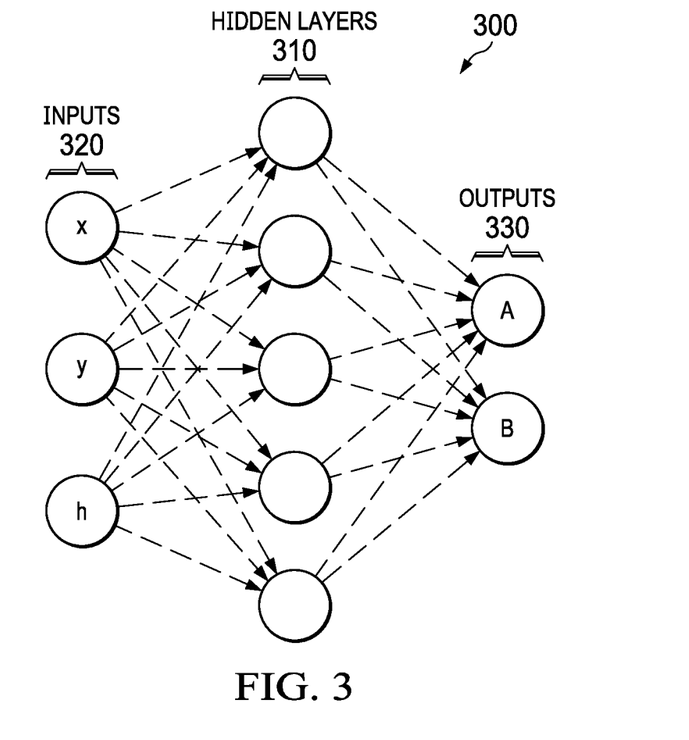
FIG. 3 is a schematic diagram illustrating an example map of critical properties of another one-step tuning method using machine-learning, according to some implementations of the present disclosure.

In some implementations, the pseudo-component database 108 and the ANN for predicting critical properties can be created using other tuning techniques such as the Pedersen splitting method, the Lohrenz splitting method, the Katz splitting method, the Whitson splitting method, and the Ahmed splitting method. For example, the Pedersen splitting method can model the mole-fraction distribution of heavy fractions using an exponential function $$z_n = e^{A+B \cdot MW_n}, \quad (5)$$

where $MW_n$ represents the molecular weight and $z_n$ represents the mole-fraction of the heavy component whose CN is n. Parameters A and B are obtained by region-specific tuning of the EOS. Parameters A and B represent fitting parameters that describe the distribution of heavy pure components in the lumped pseudo-components. In some cases, the heavy components are those with CN greater than 10. An example 3D map can be obtained using an ANN regression shown in FIG. 3.

FIG. 3 is a schematic diagram illustrating an example map 300 of critical properties of another one-step tuning method using machine-learning, according to some implementations of the present disclosure. The input 320 to the hidden layers 310 of machine-learning algorithm (for example, ANN) are spatial coordinates x, y, and h of the corresponding well location in the reservoir. The output 330 of the critical properties, A and B, is calculated using ANN regression. The mole-fraction distribution for the heavy components can be obtained using equation (5). The critical properties $T_c$, $P_c$, and $\omega$ of the pseudo-components can be obtained from mixing rules using the mole-fraction distribution of heavy components. The machine-learning algorithm 310 can capture the changes in the distribution of heavy fractions across the reservoir due to the compartmentalization of components across the reservoir.

At 114, the results of the EOS tuning are used to create a map of the critical properties of the pseudo-components ($T_c(x, y, h)$ and $P_c(x, y, h)$ and $\omega(x, y, h)$) using machine-learning techniques such as ANN and least square support vector machines (LS-SVM), or other techniques that include machine-learning-based regression analysis. From 114, method 100 proceeds to 116.

At 116, a reservoir-specific compositional map is created. In some implementations, the reservoir-specific compositional map is created by performing a spatial mapping of compositions across the reservoir. The spatial mapping can be performed in two steps. First, available data on compositional analysis of downhole fluids are collected from various well locations or regions in the reservoir. Second, interpolations using techniques that are thermodynamically consistent can be performed between the sampled locations. As such, the compositional map created is specific to the reservoir.

For example, an interpolation technique can be performed along the depth h of a surface using an inverse distance weighting (IDW) method. Using IDW, mole fraction $z_i$ of component i at a spatial location (x, y) can be expressed as:

$$z_i = \frac{\sum_{k=1}^{N} w_k z_{i,k}}{\sum_{k=1}^{N} w_k}, \quad (6)$$

where N is the number of sampled well locations or regions, and $w_k$ is a IDW function that can be expressed as $$w_k = \frac{1}{\left(\sqrt{(x-x_k)^2 + (y-y_k)^2}\right)^p}, \quad (7)$$

$z_{i,k}$ is the mole fraction of component i sampled at location k with spatial coordinates given by $(x_k, y_k, h)$, and p=2, where p represents power parameter that determines the maximum distance over which the individual data point exerts influence over other data points. The principle of thermal equilibrium can be used for obtaining the compositions along the depth h at location (x, y) to provide thermodynamic consistency. In some implementations, the fluid in the pores can be connected and influenced by gravity induced compositional gradients. Therefore, based on information of overall composition at a depth $h_0$, the overall composition at depth h can be calculated by using the equality of chemical potentials along the depth expressed as $$\mu_i(h) - \mu_i(h_0) = M_i \cdot g \cdot (h - h_0) \quad (8),$$

The chemical potential $\mu_i$ of component i is a function of pressure, temperature, and the overall fluid composition, where a hydrostatic pressure head is assumed for the variation of pressure along the depth. $M_i$ represents the molecular weight of the component i. The chemical potentials are obtained using the region-specific tuned EOS, where g represents gravitational acceleration constant. As such, a reservoir-specific compositional map is created using a combination of interpolation techniques and the principle of thermal equilibrium. From 116, method 100 proceeds to 118.

At 118, simulations of DL, CVD, CME, or swelling tests can be used to create a reservoir-specific compositional database 120. The reservoir-specific compositional database 120 can be generated based on a reservoir-specific compositional map. The reservoir-specific compositional database can be used to train the machine-learning algorithm for making predictions on phase stability and perform flash calculations for compositional reservoir simulations. The development of the compositional database can depend on the nature of the oil recovery process. For example, in a water-flooding process, oils can be displaced by water and undergo compositional changes due to depletion processes. Moreover, oils of a specific region can be mixed with oils (in liquid or vapor phases) from neighboring regions.

In some implementations, a DL test can describe the depletion processes that occur in an oil reservoir (for a gas reservoir, a CVD test can be used). The changes to the overall composition that occur due to the depletion processes in the oil reservoir can be captured by simulating a DL test. The DL test can be simulated for the spatially mapped compositions (including sampled and interpolated compositions) using region-specific tuned EOS. The fluid compositions at all stages of the DL test in the reservoir-specific compositional database can be stored. Moreover, at each stage of the DL test, additional overall fluid compositions that result from accumulation or depletion of liquid or vapor phases can be stored from previous stages using a mole balance for each component. The overall fluid composition of component i after addition or depletion of liquid or vapor phases can be expressed as:

$$z_i^m = \frac{z_i - x_i \cdot (1-\beta) \cdot f_l - y_i \cdot \beta \cdot f_g}{(1 - \beta \cdot f_g - (1-\beta) \cdot f_l)}, \quad (9)$$

where $x_i$ is the mole-fraction of liquid phase that is added or depleted, $\beta$ is the vapor phase fraction, $f_l$ is the fraction of liquid phase that is either added or depleted, $y_i$ is the mole-fraction of vapor phase that is either added or depleted, $f_g$ is the fraction of vapor phase that is either added or depleted, and $z_i$ is the overall composition of the fluid at a given stage of the DL test. The liquid compositions $x_i$ and vapor compositions $y_i$ are obtained using flash calculations at each stage of the DL test. Moreover, $f_l$ and $f_g$ can be varied from −1 to 1 (at each stage of DL test) and the overall compositions can be obtained using equation (9) under the constraint that $\Sigma_{i=1}^{N_c} z_i^m = 1$, where $N_C$ is the number of components. Equation (9) can be used to obtain compositions in a neighborhood of the original composition and to expand the training domain of the supervised learning algorithm. The compositions can be stored in the reservoir-specific compositional database 120, which can then be used to train the machine-learning algorithm. From 120, method 100 proceeds to 122.

At 122, the machine-learning algorithm is trained for phase stability testing and flash calculations using the reservoir-specific compositional database 120 and the region-specific tuned EOS. The machine-learning algorithm can be trained using the reservoir-specific compositional database 120 and the region-wise tuned EOS at 106. In some implementations, the reservoir is partitioned into grid blocks and the discretized partial differential equations (PDEs) are solved for compositional reservoir simulation. The PDEs can capture the compositional flow through porous media. Machine-learning algorithm can be used as a surrogate model for flash calculations in the compositional reservoir simulations. The algorithm can use the overall composition, pressure, temperature and the corresponding spatial coordinates of the grid block as input. The spatial coordinates can be used to determine the pseudo-components that represent heavy fractions. In some implementations, a variation in the distribution of the heavy fractions across the reservoir exist and region-specific tuning of EOS can be performed to capture the variation.

Figure 4:
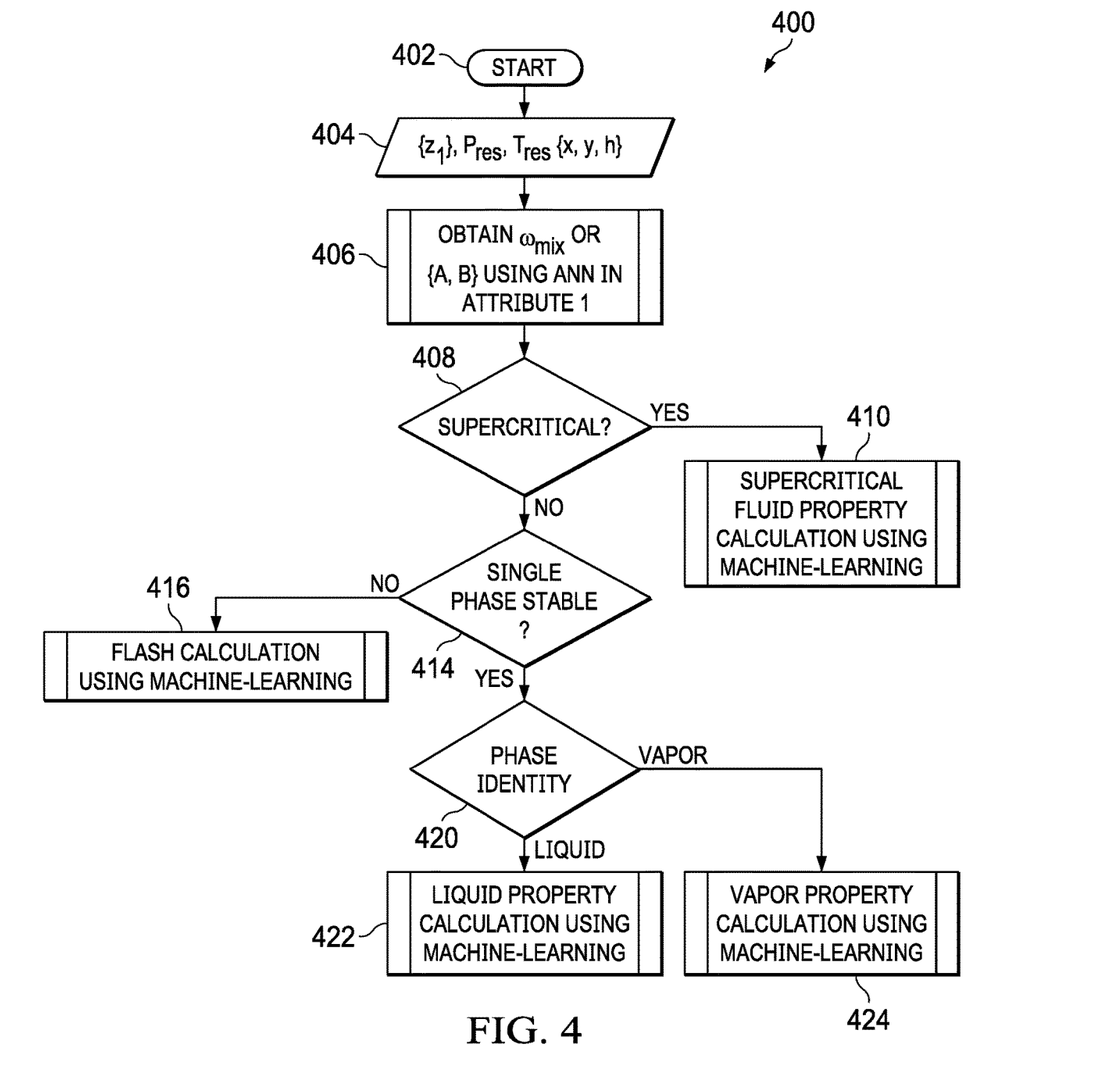
FIG. 4 is a flowchart illustrating an example method for developing a machine-learning based surrogate model for both supercritical and sub-critical phase behaviors, according to some implementations of the present disclosure.

Referring to FIG. 4, FIG. 4 is a flowchart illustrating an example method 400 for developing a machine-learning based surrogate model for both supercritical and sub-critical phase behaviors, according to some implementations of the present disclosure. At a high-level, the method 400 includes a combination of classification and regression. The method 400 starts at 402. At 404, critical properties, including critical temperature ($T_{res}$), critical pressure ($P_{res}$), and a set of mole fractions of each component ($\{z_i\}$) are calculated for a specific region with spatial coordinates $\{x, y, h\}$, as discussed in the description of 114 and 116 of FIG. 1. At 406, the acentric factor $\omega_{mix}$ of a mixture of more than one pseudo-component or $\{A, B\}$ can be obtained using an ANN as discussed in the descriptions of FIGS. 2 and 3, where A and B represent fitting parameters that can describe the distribution of heavy pure components included in the mixture of more than one pseudo-component. At 408, it is determined whether the fluid is in supercritical state. If yes, the super-critical fluid properties are calculated using machine-learning at 410. After 410, method 400 stops at 412. Otherwise, it is determined whether a single phase is stable at 414. If the single phase is found to be unstable at 414, flash calculation is performed using machine-learning to calculate phase equilibrium for compositional modeling at 416. After 416, method 400 stops at 418. Otherwise, phase identities are identified at 420. The phases can be classified into a liquid phase and a vapor phase if two subcritical phases are identified. The liquid-phase properties are calculated using machine-learning at 422 and the vapor phase properties are calculated using machine-learning at 424. After 422 or 424, method 400 stops at 426.

The method 400 can improve the accuracy of the compositional reservoir simulations by using spatial coordinates and reservoir-specific compositional databases. In some implementations, the decision-making at 408, 414, and 420 can be performed by a supervised machine-learning algorithm for classification. Other calculation steps can be performed using an supervised machine-learning algorithm for regression For fluids that include only sub-critical phases, the following algorithm can be used for stability analysis and phase-split calculations at the current time-step t. The phase state of the given grid-block at the previous time-step (t−1).

1. Obtain machine-learning based surrogate models for parameters including the bubble-point ($P_b$) and dew-point ($P_d$) of the hydrocarbon fluid, the distribution coefficients of all the components (equilibrium $K_i$ values), the vapor-split fraction ($\beta$), the liquid compressibility factor ($Z_L$), and the gas compressibility factor ($Z_G$).

The surrogate models can be expressed as, $$P_b = f_1(\{z_i\}, T) \quad (10),$$

$$P_d = f_2(\{z_i\}, T) \quad (11),$$

$$K_i = f_3(\{z_i\}, T) \quad (12),$$

$$\beta = f_4(\{z_i\}, \{K_i\}, T) \quad (13),$$

$$Z_L = f_5(\{x_i\}, T) \quad (14),$$

$$Z_G = f_6(\{y_i\}, T) \quad (15).$$

where $z_i$ is the overall composition (i=1 to $n_c$, where $n_c$ is the total number of components), T is the temperature, $x_i$ is the composition of liquid phase, and $y_i$ is the composition of vapor phase. The surrogate models $\{f_i\}_{i=1 \text{ to } 6}$ can be obtained from machine-learning techniques for regression such as ANN and support vector regression. In some cases, it is not necessary to have 0<$\beta$<1 while developing surrogate models $f_3$ and $f_4$.

2. Use the information from the previous time-step t−1 to check if a hydrocarbon phase was in a single phase region or a two-phase region at time-step t−1. If it was in a single-phase region, then check if the phase was liquid or vapor.

3. If at time-step t−1, the grid-block was in liquid phase, then use the machine-learning based surrogate model (equation (10)) to calculate the bubble point of the fluid at the current time step ($P_b^t$) using the overall composition and temperature at the current time-step t, and check if $P^t < P_b^t$. If yes, then proceed to perform phase-split calculations. Otherwise, label the current state of the grid-block as liquid and proceed to thermodynamic property evaluation for the liquid phase.

4. If at previous time-step t−1, the grid-block was in a vapor phase, use the machine-learning based surrogate model (equation (11)) to obtain the dew-point of the fluid $P_d^t$ at the current time-step t using the overall composition and temperature at the current time-step t, and check if $P^t < P_d^t$. If yes, then proceed to perform phase-split calculations. Otherwise, label the current state of the grid-block as gas and proceed to thermodynamic property evaluation for the gas phase.

5. If at the previous time-step t−1, the grid-block was in two-phases, obtain the equilibrium distribution coefficients $K_i$ using the machine-learning based surrogate model (equation (12)). Obtain the vapor-split fraction using the machine-learning based surrogate model (equation (13)).

6. Check if 0<β<1. If yes, then proceed to the calculation of thermodynamic properties and their derivatives. Otherwise, check if β<0. If yes, label the current state of the grid-block as liquid and proceed to thermodynamic property calculation. Check if β>1. If yes, label the current state of the grid-block as gas and then proceed to thermodynamic property calculation of the gas phase.

7. Obtain the thermodynamic properties. Surrogate model $f_5$ can be used for calculating the liquid densities, while surrogate model $f_6$ is used for gas densities. The viscosities of the phases can be obtained from analytical expressions of viscosity as a function of phase densities.

8. Obtain the derivatives of the thermodynamic properties using analytical expressions and calculated values of thermodynamic properties from step 7. The derivatives can also be obtained from the trained machine-learning-based surrogate models.

9. Construct the Jacobian matrix and calculate the residuals using the obtained thermodynamic properties and their derivatives from steps 7 and 8.

Figure 5:
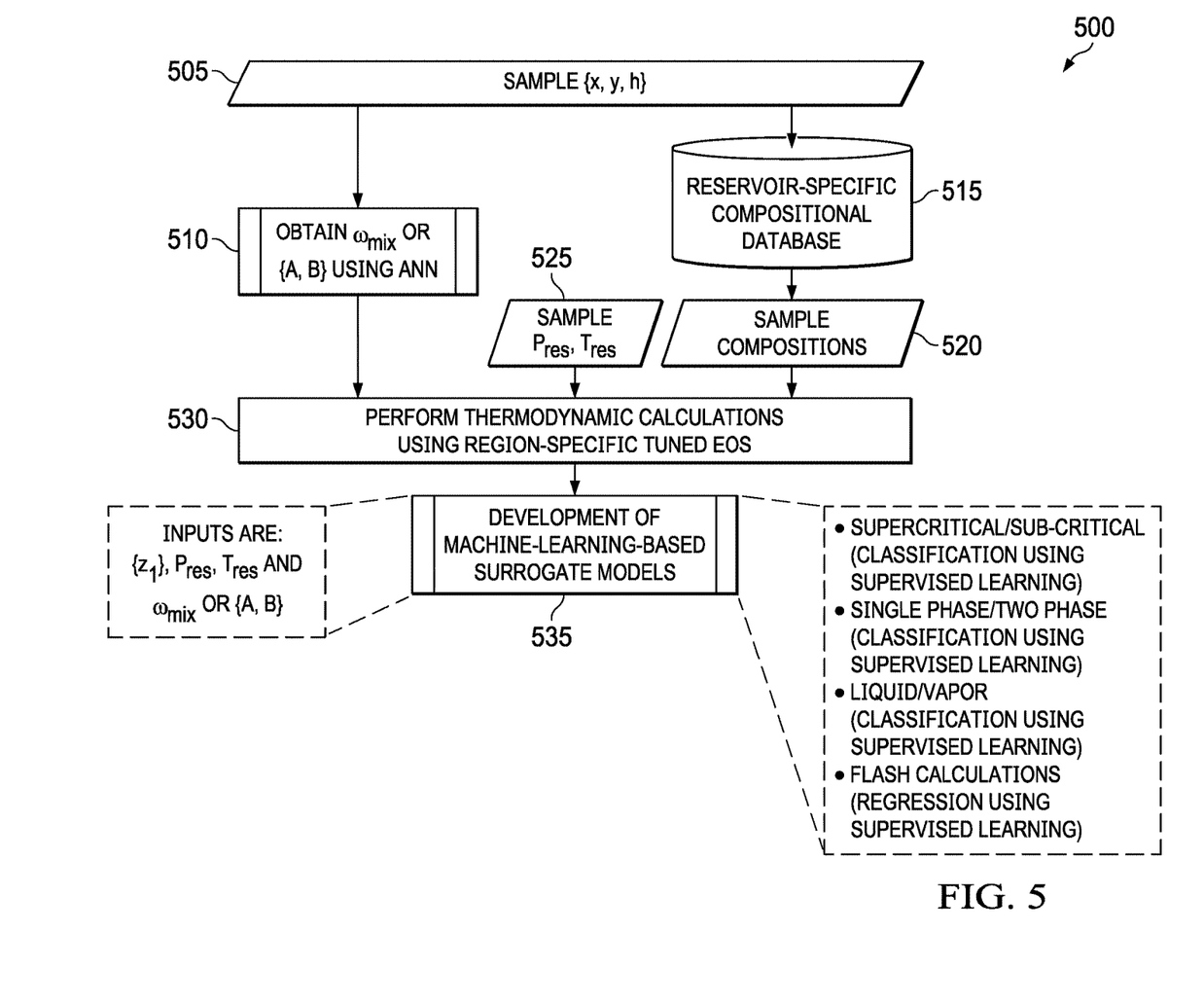
FIG. 5 is a schematic diagram illustrating an example of development of surrogate models for compositional simulations using different machine-learning algorithms, according to some implementations of the present disclosure.

Referring to FIG. 5, FIG. 5 is a schematic diagram illustrating an example 500 of development of surrogate models for compositional simulations using different machine-learning algorithms, according to some implementations of the present disclosure. At 505, the corresponding spatial coordinates of all the grid blocks {x, y, h} in the reservoir are sampled. At 520, compositions that fall in the neighborhood of sampled spatial coordinates are queried from the reservoir-specific compositional database 515. The results of the DL tests simulated using the queried compositions are also obtained from the database. At 510, the acentric factor $\omega_{mix}$ of a pseudo-component or {A, B} can be obtained using an ANN as discussed in the descriptions of FIGS. 2 and 3. At 525, the reservoir properties, including reservoir temperature $T_{res}$ and reservoir pressure $P_{res}$ are sampled at different regions of the reservoir. At 530, thermodynamic calculations are performed using region-specific tuned EOS. At 535, the results of the thermodynamic calculations are used to train the machine-learning based surrogate model. The input to the machine-learning algorithm can include reservoir temperature $T_{res}$, reservoir pressure $P_{res}$, a set of mole fractions of the components {$z_i$} that represent the overall composition, the acentric factor $\omega_{mix}$ of pseudo-component or {A, B}. The output of the machine-learning algorithm can include a classification of supercritical and subcritical phases, a classification of single phase and two phases using supervised machine-learning if the fluid composition is subcritical, a classification of liquid and vapor using supervised machine-learning, and flash calculations including regression using supervised machine-learning if a single phase is unstable.

The supervised algorithm can predict the equilibrium K values (distribution coefficients) of component i. The input for both supervised machine-learning algorithms are the set of mole fractions of components {$z_i$}, the reservoir pressure $P_{res}$, the reservoir temperature $T_{res}$ and a parameter that can quantify the distribution of heavy fractions in the reservoir (for example, $\omega_{mix}$ or {A, B}). In some implementations, the results of the machine-learning algorithm can also be used to generate initial guesses close to the actual solution for performing thermodynamic calculations Referring back to FIG. 1, at 124, compositional reservoir simulations are performed based on the machine-learning-based surrogate models. After 124, method 100 stops at 126.

Figure 6:
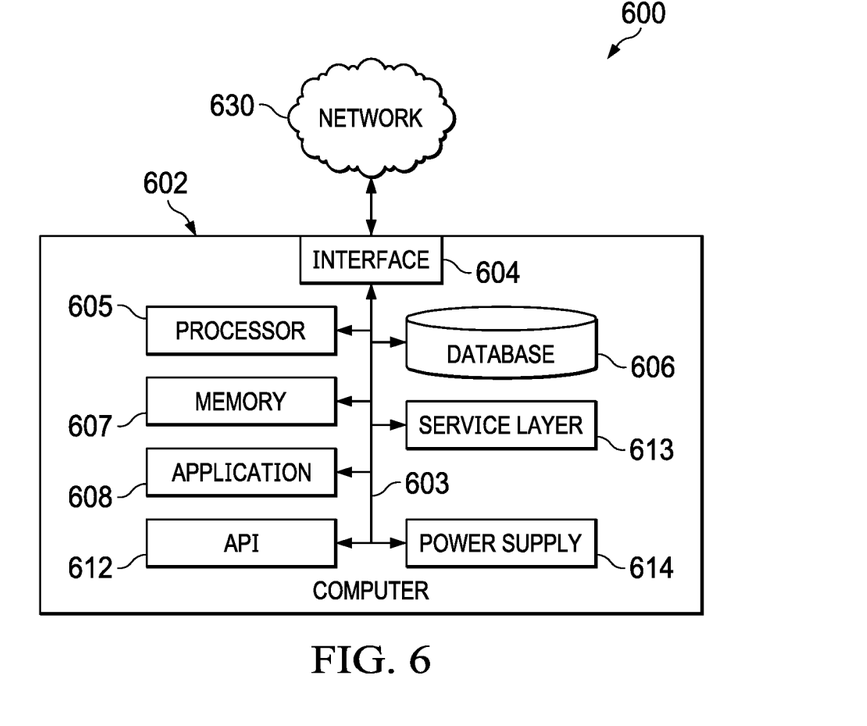
FIG. 6 is a block diagram illustrating an example computer system used to provide computational functionalities associated with described algorithms, methods, functions, processes, flows, and procedures as described in the instant disclosure, according to some implementations of the present disclosure.

FIG. 6 is a block diagram of an example computer system 600 used to provide computational functionalities associated with described algorithms, methods, functions, processes, flows, and procedures, as described in the instant disclosure, according to an implementation. The illustrated computer 602 is intended to encompass any computing device such as a server, desktop computer, laptop/notebook computer, wireless data port, smart phone, personal data assistant (PDA), tablet computing device, one or more processors within these devices, or any other suitable processing device, including physical or virtual instances (or both) of the computing device. Additionally, the computer 602 can comprise a computer that includes an input device, such as a keypad, keyboard, touch screen, or other device that can accept user information, and an output device that conveys information associated with the operation of the computer 602, including digital data, visual, or audio information (or a combination of information), or a graphical-type user interface (UI) (or GUI).

The computer 602 can serve in a role as a client, network component, a server, a database or other persistency, or any other component (or a combination of roles) of a computer system for performing the subject matter described in the instant disclosure. The illustrated computer 602 is communicably coupled with a network 630. In some implementations, one or more components of the computer 602 can be configured to operate within environments, including cloud-computing-based, local, global, or other environment (or a combination of environments).

At a high level, the computer 602 is an electronic computing device operable to receive, transmit, process, store, or manage data and information associated with the described subject matter. According to some implementations, the computer 602 can also include or be communicably coupled with an application server, e-mail server, web server, caching server, streaming data server, or other server (or a combination of servers).

The computer 602 can receive requests over network 630 from a client application (for example, executing on another computer 602) and respond to the received requests by processing the received requests using an appropriate software application(s). In addition, requests can also be sent to the computer 602 from internal users (for example, from a command console or by other appropriate access method), external or third-parties, other automated applications, as well as any other appropriate entities, individuals, systems, or computers.

Each of the components of the computer 602 can communicate using a system bus 603. In some implementations, any or all of the components of the computer 602, hardware or software (or a combination of both hardware and software), can interface with each other or the interface 604 (or a combination of both), over the system bus 603 using an application programming interface (API) 612 or a service layer 613 (or a combination of the API 612 and service layer 613). The API 612 can include specifications for routines, data structures, and object classes. The API 612 can be either computer-language independent or dependent and refer to a complete interface, a single function, or even a set of APIs. The service layer 613 provides software services to the computer 602 or other components (whether or not illustrated) that are communicably coupled to the computer 602. The functionality of the computer 602 can be accessible for all service consumers using this service layer. Software services, such as those provided by the service layer 613, provide reusable, defined functionalities through a defined interface. The interface can be software written in JAVA, C++, or other suitable language providing data in extensible markup language (XML) format or other suitable format. While illustrated as an integrated component of the computer 602, alternative implementations can illustrate the API 612 or the service layer 613 as stand-alone components in relation to other components of the computer 602 or other components (whether or not illustrated) that are communicably coupled to the computer 602. Moreover, any or all parts of the API 612 or the service layer 613 can be implemented as child or sub-modules of another software module, enterprise application, or hardware module without departing from the scope of this disclosure.

The computer 602 includes an interface 604. Although illustrated as a single interface 604 in FIG. 6, two or more interfaces 604 can be used according to particular needs, desires, or particular implementations of the computer 602. The interface 604 is used by the computer 602 for communicating with other systems that are connected to the network 630 (whether illustrated or not) in a distributed environment. Generally, the interface 604 comprises logic encoded in software or hardware (or a combination of software and hardware) and is operable to communicate with the network 630. More specifically, the interface 604 can comprise software supporting one or more communication protocols associated with communications such that the network 630 or interface's hardware is operable to communicate physical signals within and outside of the illustrated computer 602.

The computer 602 includes a processor 605. Although illustrated as a single processor 605 in FIG. 6, two or more processors can be used according to particular needs, desires, or particular implementations of the computer 602. Generally, the processor 605 executes instructions and manipulates data to perform the operations of the computer 602 and any algorithms, methods, functions, processes, flows, and procedures as described in the instant disclosure.

The computer 602 also includes a database 606 that can hold data for the computer 602 or other components (or a combination of both) that can be connected to the network 630 (whether illustrated or not). For example, database 606 can be an in-memory, conventional, or other type of database storing data consistent with this disclosure. In some implementations, database 606 can be a combination of two or more different database types (for example, a hybrid in-memory and conventional database) according to particular needs, desires, or particular implementations of the computer 602 and the described functionality. Although illustrated as a single database 606 in FIG. 6, two or more databases (of the same or combination of types) can be used according to particular needs, desires, or particular implementations of the computer 602 and the described functionality. While database 606 is illustrated as an integral component of the computer 602, in alternative implementations, database 606 can be external to the computer 602.

The computer 602 also includes a memory 607 that can hold data for the computer 602 or other components (or a combination of both) that can be connected to the network 630 (whether illustrated or not). Memory 607 can store any data consistent with this disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 6, two or more memories 607 (of the same or combination of types) can be used according to particular needs, desires, or particular implementations of the computer 602 and the described functionality. While memory 607 is illustrated as an integral component of the computer 602, in alternative implementations, memory 607 can be external to the computer 602.

The application 608 is an algorithmic software engine providing functionality according to particular needs, desires, or particular implementations of the computer 602, particularly with respect to functionality described in this disclosure. For example, application 608 can serve as one or more components, modules, or applications. Further, although illustrated as a single application 608, the application 608 can be implemented as multiple applications 608 on the computer 602. In addition, although illustrated as integral to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion or management circuits (including recharging, standby, or other power management functionality). In some implementations, the power-supply 614 can include a power plug to allow the computer 602 to be plugged into a wall socket or other power source to, for example, power the computer 602 or recharge a rechargeable battery.

There can be any number of computers 602 associated with, or external to, a computer system containing computer 602, each computer 602 communicating over network 630. Further, the term "client," "user," and other appropriate terminology can be used interchangeably, as appropriate, without departing from the scope of this disclosure. Moreover, this disclosure contemplates that many users can use one computer 602, or that one user can use multiple computers 602.

Described implementations of the subject matter can include one or more features, alone or in combination.

For example, in a first implementation, a computer-implemented method, comprising: determining an equation of state (EOS) for each of one or more regions of a reservoir based on results of one or more pressure, volume, or temperature (PVT) experiments conducted on samples of downhole fluids obtained from one or more regions of the reservoir; determining compositions of the samples of the downhole fluids; spatially mapping the determined compositions of the samples of the downhole fluids based on interpolations between the one or more regions of the reservoir; simulating one or more PVT experiments for the spatially mapped compositions of the downhole fluids using the determined EOS to create a compositional database of the reservoir; training one or more machine-learning algorithms using the compositional database; and using the trained one or more machine-learning algorithms to predict phase stability and perform flash calculations for compositional reservoir simulation.

The foregoing and other described implementations can each, optionally, include one or more of the following features:

A first feature, combinable with any of the following features, wherein the one or more PVT experiments include at least one of a differential liberation test, a constant mass expansion test, a constant vapor depletion test, a swelling test, or fluid density measurements.

A second feature, combinable with any of the previous or following features, wherein determining the EOS includes determining critical properties of one or more pseudo-components of the downhole fluid by regressing data from the PVT experiments.

A third feature, combinable with any of the previous or following features, wherein the critical properties include at least one of critical temperature, critical pressure, or acentric factor, and wherein the acentric factor is determined based on spatial coordinates of the corresponding region of the downhole fluid.

A fourth feature, combinable with any of the previous or following features, wherein the acentric factor is determined for a plurality of heavy pseudo-components or parameters describing distribution of the plurality of heavy components, and wherein each heavy pseudo-component has a carbon number greater than or equal to 10.

A fifth feature, combinable with any of the previous or following features, wherein determining critical properties further includes using at least one of an artificial neural network or a least square support vector machine algorithm to determine the acentric factor.

A sixth feature, combinable with any of the previous or following features, further comprising storing the determined compositions and compositions generated by simulating the one or more PVT experiments to the compositional database.

A seventh feature, combinable with any of the previous or following features, wherein the interpolations are performed between the one or more regions along a surface of constant depth using an inverse distance weighting method.

An eighth feature, combinable with any of the previous or following features, wherein spatially mapping the determined compositions of the downhole fluid includes calculating compositions using the equality of chemical potentials between a depth of the corresponding region and a depth of a different region of the reservoir where an overall composition is known.

A ninth feature, combinable with any of the previous or following features, further comprising: creating a pseudo-component database for each of the one or more region of the reservoir, wherein the pseudo-component database is used for PVT property prediction and analysis.

In a second implementation, a non-transitory, computer-readable medium storing one or more instructions executable by a computer system to perform operations comprising: determining an equation of state (EOS) for each of one or more regions of a reservoir based on results of one or more pressure, volume, or temperature (PVT) experiments conducted on samples of downhole fluids obtained from one or more regions of the reservoir; determining compositions of the samples of the downhole fluids; spatially mapping the determined compositions of the samples of the downhole fluids based on interpolations between the one or more regions of the reservoir; simulating one or more PVT experiments for the spatially mapped compositions of the downhole fluids using the determined EOS to create a compositional database of the reservoir; training one or more machine-learning algorithms using the compositional database; and using the trained one or more machine-learning algorithms to predict phase stability and perform flash calculations for compositional reservoir simulation.

The foregoing and other described implementations can each, optionally, include one or more of the following features:

A first feature, combinable with any of the following features, wherein the one or more PVT experiments include at least one of a differential liberation test, a constant mass expansion test, a constant vapor depletion test, a swelling test, or fluid density measurements.

A second feature, combinable with any of the previous or following features, wherein determining the EOS includes determining critical properties of one or more pseudo-components of the downhole fluid by regressing data from the PVT experiments.

A third feature, combinable with any of the previous or following features, wherein the critical properties include at least one of critical temperature, critical pressure, or acentric factor, and wherein the acentric factor is determined based on spatial coordinates of the corresponding region of the downhole fluid.

A fourth feature, combinable with any of the previous or following features, wherein the acentric factor is determined for a plurality of heavy pseudo-components or parameters describing distribution of the plurality of heavy components, and wherein each heavy pseudo-component has a carbon number greater than or equal to 10.

A fifth feature, combinable with any of the previous or following features, wherein determining critical properties further includes using at least one of an artificial neural network or a least square support vector machine algorithm to determine the acentric factor.

A sixth feature, combinable with any of the previous or following features, further comprising storing the determined compositions and compositions generated by simulating the one or more PVT experiments to the compositional database.

A seventh feature, combinable with any of the previous or following features, wherein the interpolations are performed between the one or more regions along a surface of constant depth using an inverse distance weighting method.

An eighth feature, combinable with any of the previous or following features, wherein spatially mapping the determined compositions of the downhole fluid includes calculating compositions using the equality of chemical potentials between a depth of the corresponding region and a depth of a different region of the reservoir where an overall composition is known.

A ninth feature, combinable with any of the previous or following features, further comprising: creating a pseudo-component database for each of the one or more region of the reservoir, wherein the pseudo-component database is used for PVT property prediction and analysis.

In a third implementation, A computer-implemented system, comprising: one or more computers; and one or more computer memory devices interoperably coupled with the one or more computers and having tangible, non-transitory, machine-readable media storing instructions that, when executed by the one or more computers, perform operations comprising: determining an equation of state (EOS) for each of one or more regions of a reservoir based on results of one or more pressure, volume, or temperature (PVT) experiments conducted on samples of downhole fluids obtained from one or more regions of the reservoir; determining compositions of the samples of the downhole fluids; spatially mapping the determined compositions of the samples of the downhole fluids based on interpolations between the one or more regions of the reservoir; simulating one or more PVT experiments for the spatially mapped compositions of the downhole fluids using the determined EOS to create a compositional database of the reservoir; training one or more machine-learning algorithms using the compositional database; and using the trained one or more machine-learning algorithms to predict phase stability and perform flash calculations for compositional reservoir simulation.

The foregoing and other described implementations can each, optionally, include one or more of the following features:

A first feature, combinable with any of the following features, wherein the one or more PVT experiments include at least one of a differential liberation test, a constant mass expansion test, a constant vapor depletion test, a swelling test, or fluid density measurements.

A second feature, combinable with any of the previous or following features, wherein determining the EOS includes determining critical properties of one or more pseudo-components of the downhole fluid by regressing data from the PVT experiments.

A third feature, combinable with any of the previous or following features, wherein the critical properties include at least one of critical temperature, critical pressure, or acentric factor, and wherein the acentric factor is determined based on spatial coordinates of the corresponding region of the downhole fluid.

A fourth feature, combinable with any of the previous or following features, wherein the acentric factor is determined for a plurality of heavy pseudo-components or parameters describing distribution of the plurality of heavy components, and wherein each heavy pseudo-component has a carbon number greater than or equal to 10.

A fifth feature, combinable with any of the previous or following features, wherein determining critical properties further includes using at least one of an artificial neural network or a least square support vector machine algorithm to determine the acentric factor.

A sixth feature, combinable with any of the previous or following features, further comprising storing the determined compositions and compositions generated by simulating the one or more PVT experiments to the compositional database.

A seventh feature, combinable with any of the previous or following features, wherein the interpolations are performed between the one or more regions along a surface of constant depth using an inverse distance weighting method.

An eighth feature, combinable with any of the previous or following features, wherein spatially mapping the determined compositions of the downhole fluid includes calculating compositions using the equality of chemical potentials between a depth of the corresponding region and a depth of a different region of the reservoir where an overall composition is known.

A ninth feature, combinable with any of the previous or following features, further comprising: creating a pseudo-component database for each of the one or more region of the reservoir, wherein the pseudo-component database is used for PVT property prediction and analysis.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 ms, less than 1 sec., or less than 5 secs. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, LINUX, UNIX, WINDOWS, MAC OS, ANDROID, IOS, or any other suitable conventional operating system.

A computer program, which can also be referred to or described as a program, software, a software application, a module, a software module, a script, or code can be written in any form of programming language, including compiled or interpreted languages, or declarative or procedural languages, and it can be deployed in any form, including as a stand-alone program or as a module, component, subroutine, or other unit suitable for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures are shown as individual modules that implement the various features and functionality through various objects, methods, or other processes, the programs can instead include a number of sub-modules, third-party services, components, libraries, and such, as appropriate. Conversely, the features and functionality of various components can be combined into single components, as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data includes all forms of permanent/non-permanent or volatile/non-volatile memory, media and memory devices, including by way of example semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices; magnetic devices, tape, cartridges, cassettes, internal/removable disks; magneto-optical disks; and optical memory devices, for example, digital video disc (DVD), CD-ROM, DVD+/-R, DVD-RAM, DVD-ROM, HD-DVD, and BLURAY, and other optical memory technologies. The memory can store various objects or data, including caches, classes, frameworks, applications, modules, backup data, jobs, web pages, web page templates, data structures, database tables, repositories storing dynamic information, and any other appropriate information including any parameters, variables, algorithms, instructions, rules, constraints, or references. Additionally, the memory can include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with this disclosure), all or a portion of the Internet, or any other communication system or systems at one or more locations (or a combination of communication networks). The network can communicate with, for example, Internet Protocol (IP) packets, Frame Relay frames, Asynchronous Transfer Mode (ATM) cells, voice, video, data, or other suitable information (or a combination of communication types) between network addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any implementations or on the scope of what can be claimed, but rather as descriptions of features that can be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain this disclosure. Other changes, substitutions, and alterations are also possible without departing from the spirit and scope of this disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A computer-implemented method, comprising:
    determining an equation of state (EOS) for each of one or more regions of a reservoir based on results of one or more pressure, volume, or temperature (PVT) experiments conducted on samples of downhole fluids obtained from one or more regions of the reservoir;
    determining compositions of the samples of the downhole fluids;
    spatially mapping the determined compositions of the samples of the downhole fluids based on interpolations between the one or more regions of the reservoir;
    simulating one or more PVT experiments for the spatially mapped compositions of the downhole fluids using the determined EOS to create a compositional database of the reservoir;
    training one or more machine-learning algorithms using the compositional database; and
    using the trained one or more machine-learning algorithms to non-iteratively predict phase stability and perform non-iterative flash calculations for compositional reservoir simulation.

2. The computer-implemented method of claim 1, wherein the one or more PVT experiments include at least one of a differential liberation test, a constant mass expansion test, a constant vapor depletion test, a swelling test, or fluid density measurements.

3. The computer-implemented method of claim 1, wherein determining the EOS includes determining critical properties of one or more pseudo-components of the downhole fluid by regressing data from the PVT experiments.

4. The computer-implemented method of claim 3, wherein the critical properties include at least one of critical temperature, critical pressure, or acentric factor, and wherein the acentric factor is determined based on spatial coordinates of the corresponding region of the downhole fluid.

5. The computer-implemented method of claim 4, wherein the acentric factor is determined for a plurality of heavy pseudo-components or parameters describing distribution of the plurality of heavy components, and wherein each heavy pseudo-component has a carbon number greater than or equal to 10.

6. The computer-implemented method of claim 4, wherein determining critical properties further includes using at least one of an artificial neural network or a least square support vector machine algorithm to determine the acentric factor.

7. The computer-implemented method of claim 1, further comprising storing the determined compositions and compositions generated by simulating the one or more PVT experiments to the compositional database.

8. The computer-implemented method of claim 1, wherein the interpolations are performed between the one or more regions along a surface of constant depth using an inverse distance weighting method.

9. The computer-implemented method of claim 8, wherein spatially mapping the determined compositions of the downhole fluid includes calculating compositions using the equality of chemical potentials between a depth of the corresponding region and a depth of a different region of the reservoir where an overall composition is known.

10. The computer-implemented method of claim 1, further comprising: creating a pseudo-component database for each of the one or more region of the reservoir, wherein the pseudo-component database is used for PVT property prediction and analysis.

11. A non-transitory, computer-readable medium storing one or more instructions executable by a computer system to perform operations comprising:
- determining an equation of state (EOS) for each of one or more regions of a reservoir based on results of one or more pressure, volume, or temperature (PVT) experiments conducted on samples of downhole fluids obtained from one or more regions of the reservoir;
- determining compositions of the samples of the downhole fluids;
- spatially mapping the determined compositions of the samples of the downhole fluids based on interpolations between the one or more regions of the reservoir;
- simulating one or more PVT experiments for the spatially mapped compositions of the downhole fluids using the determined EOS to create a compositional database of the reservoir;
- training one or more machine-learning algorithms using the compositional database; and
- using the trained one or more machine-learning algorithms to non-iteratively predict phase stability and perform non-iterative flash calculations for compositional reservoir simulation.

12. The non-transitory, computer-readable medium of claim 11, wherein the one or more PVT experiments include at least one of a differential liberation test, a constant mass expansion test, a constant vapor depletion test, a swelling test, or fluid density measurements.

13. The non-transitory, computer-readable medium of claim 11, wherein determining the EOS includes determining critical properties of one or more pseudo-components of the downhole fluid by regressing data from the PVT experiments.

14. The non-transitory, computer-readable medium of claim 13, wherein the critical properties include at least one of critical temperature, critical pressure, or acentric factor, and wherein the acentric factor is determined based on spatial coordinates of the corresponding region of the downhole fluid.

15. The non-transitory, computer-readable medium of claim 11, further comprising storing the determined compositions and compositions generated by simulating the one or more PVT experiments to the compositional database.

16. A computer-implemented system, comprising:
- one or more computers; and
- one or more computer memory devices interoperably coupled with the one or more computers and having tangible, non-transitory, machine-readable media storing instructions that, when executed by the one or more computers, perform operations comprising:
  - determining an equation of state (EOS) for each of one or more regions of a reservoir based on results of one or more pressure, volume, or temperature (PVT) experiments conducted on samples of downhole fluids obtained from one or more regions of the reservoir;
  - determining compositions of the samples of the downhole fluids;
  - spatially mapping the determined compositions of the samples of the downhole fluids based on interpolations between the one or more regions of the reservoir;
  - simulating one or more PVT experiments for the spatially mapped compositions of the downhole fluids using the determined EOS to create a compositional database of the reservoir;
  - training one or more machine-learning algorithms using the compositional database; and
  - using the trained one or more machine-learning algorithms to non-iteratively predict phase stability and perform non-iterative flash calculations for compositional reservoir simulation.

17. The computer-implemented system of claim 16, wherein the one or more PVT experiments include at least one of a differential liberation test, a constant mass expansion test, a constant vapor depletion test, a swelling test, or fluid density measurements.

18. The computer-implemented system of claim 16, wherein determining the EOS includes determining critical properties of one or more pseudo-components of the downhole fluid by regressing data from the PVT experiments.

19. The computer-implemented system of claim 18, wherein the critical properties include at least one of critical temperature, critical pressure, or acentric factor, and wherein the acentric factor is determined based on spatial coordinates of the corresponding region of the downhole fluid.

20. The computer-implemented system of claim 16, further comprising storing the determined compositions and compositions generated by simulating the one or more PVT experiments to the compositional database.

* * * * *